United States Patent

Lesh et al.

Patent Number: 5,921,982
Date of Patent: Jul. 13, 1999

[54] SYSTEMS AND METHODS FOR ABLATING BODY TISSUE

[76] Inventors: Michael D. Lesh, 301 Monte Vista Ave., Mill Valley, Calif. 94941; Stuart D. Edwards, 1681 Austin Ave., Los Altos, Calif. 94024

[21] Appl. No.: 08/846,739

[22] Filed: Apr. 30, 1997

Related U.S. Application Data

[63] Continuation of application No. 08/315,396, Sep. 30, 1994, abandoned, which is a continuation-in-part of application No. 08/100,086, Jul. 30, 1993, abandoned.

[51] Int. Cl.⁶ .................................................... A61B 17/36
[52] U.S. Cl. ............................. 606/41; 606/42; 607/101; 607/122
[58] Field of Search ........................... 606/41, 42, 45–52; 607/100–102, 104, 106, 115, 116, 122, 131; 604/95; 600/374

[56] References Cited

U.S. PATENT DOCUMENTS

| | | | |
|---|---|---|---|
| 4,565,200 | 1/1986 | Cosman | 606/50 |
| 4,637,392 | 1/1987 | Sorochenko | 606/50 |
| 4,920,980 | 5/1990 | Jackowski | 604/95 |
| 4,998,933 | 3/1991 | Eggers et al. | 606/41 |
| 5,007,908 | 4/1991 | Rydell | 606/50 |
| 5,178,620 | 1/1993 | Eggers et al. | |
| 5,259,395 | 11/1993 | Li | 607/131 |
| 5,314,460 | 5/1994 | Borghi | |
| 5,314,461 | 5/1994 | Borghi | |
| 5,336,222 | 8/1994 | Durgin, Jr. et al. | 606/50 |
| 5,336,251 | 8/1994 | Borghi | |
| 5,342,357 | 8/1994 | Nardella | |
| 5,366,490 | 11/1994 | Edwards et al. | |
| 5,370,675 | 12/1994 | Edwards et al. | |
| 5,374,285 | 12/1994 | Vaiani et al. | |
| 5,383,876 | 1/1995 | Nardella | 606/50 |
| 5,385,544 | 1/1995 | Edwards et al. | |
| 5,403,311 | 4/1995 | Abele et al. | 606/50 |
| 5,405,376 | 4/1995 | Mulier et al. | |
| 5,409,453 | 4/1995 | Lundquist et al. | |
| 5,421,819 | 6/1995 | Edwards et al. | |
| 5,431,649 | 7/1995 | Mulier et al. | 128/642 |
| 5,435,805 | 7/1995 | Edwards et al. | |
| 5,470,308 | 11/1995 | Edwards et al. | |
| 5,500,012 | 3/1996 | Brucker et al. | 606/15 |
| 5,507,802 | 4/1996 | Imran | |

FOREIGN PATENT DOCUMENTS

| | | |
|---|---|---|
| 0 149 431 A2 | 7/1985 | European Pat. Off. |
| 0 452 278 A2 | 10/1991 | European Pat. Off. |
| 0 609 182 A1 | 8/1994 | European Pat. Off. |
| 0 672 431 A2 | 9/1995 | European Pat. Off. |
| 0 672 432 A1 | 9/1995 | European Pat. Off. |
| 0 452 278 B1 | 11/1995 | European Pat. Off. |

*Primary Examiner*—Michael Peffley
*Attorney, Agent, or Firm*—Lyon & Lyon LLP

[57] ABSTRACT

A medical probe device for contacting tissue within the body a catheter tube having a control end and a probe end. The probe end includes a housing having a port. An element is located within the housing that is movable between a first position confined within the housing and a second position extending through the port outside the housing. The element has a distal tip adapted to penetrate a tissue region during movement between the first and second position. The element comprises an electrode for emitting electromagnetic radio frequency energy into the tissue region, or cannula with an interior lumen for conveying fluid to and from the tissue region, or a sensor for sensing temperature conditions in the tissue region.

8 Claims, 13 Drawing Sheets

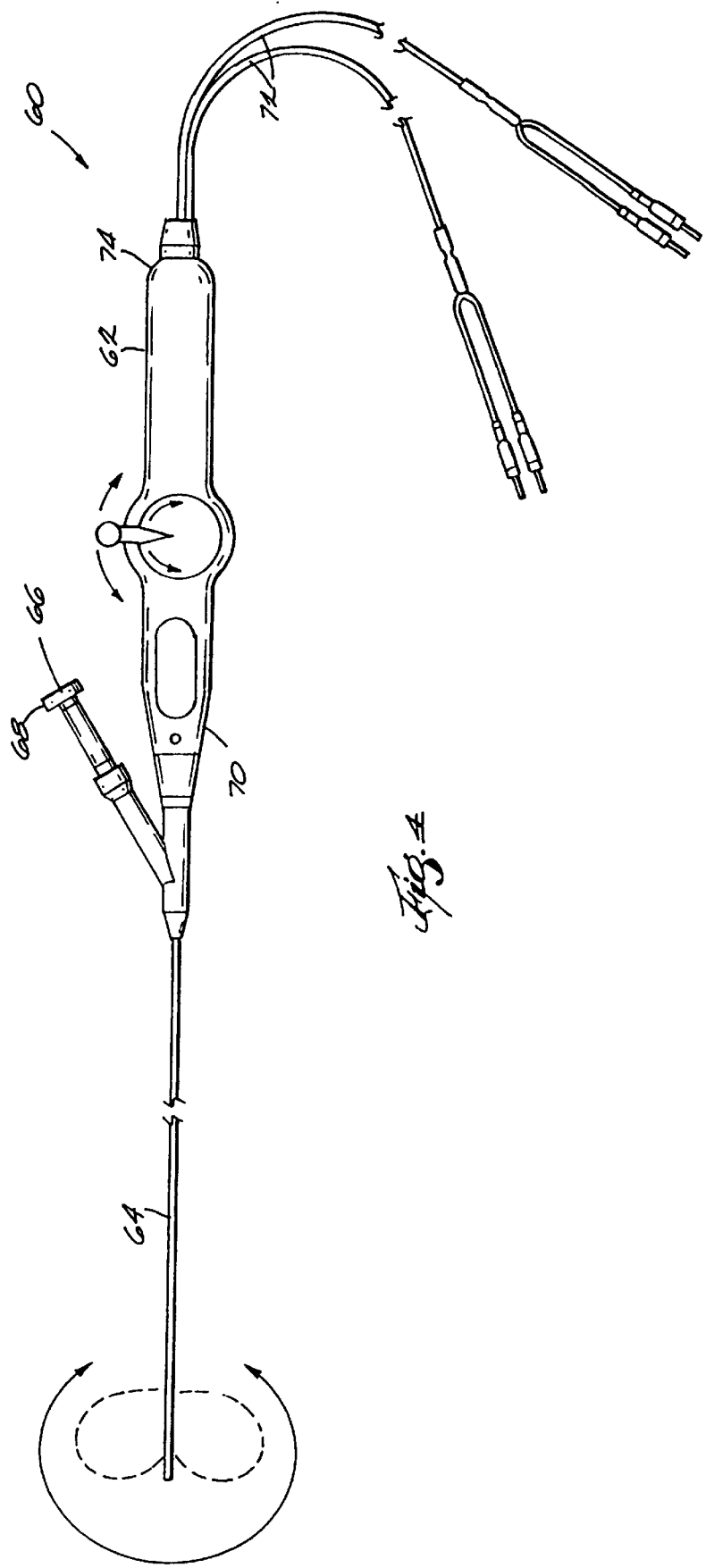

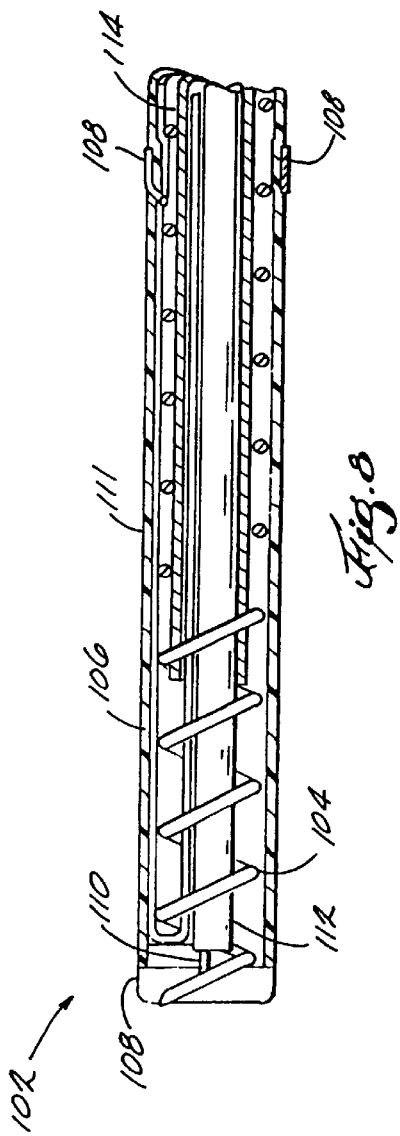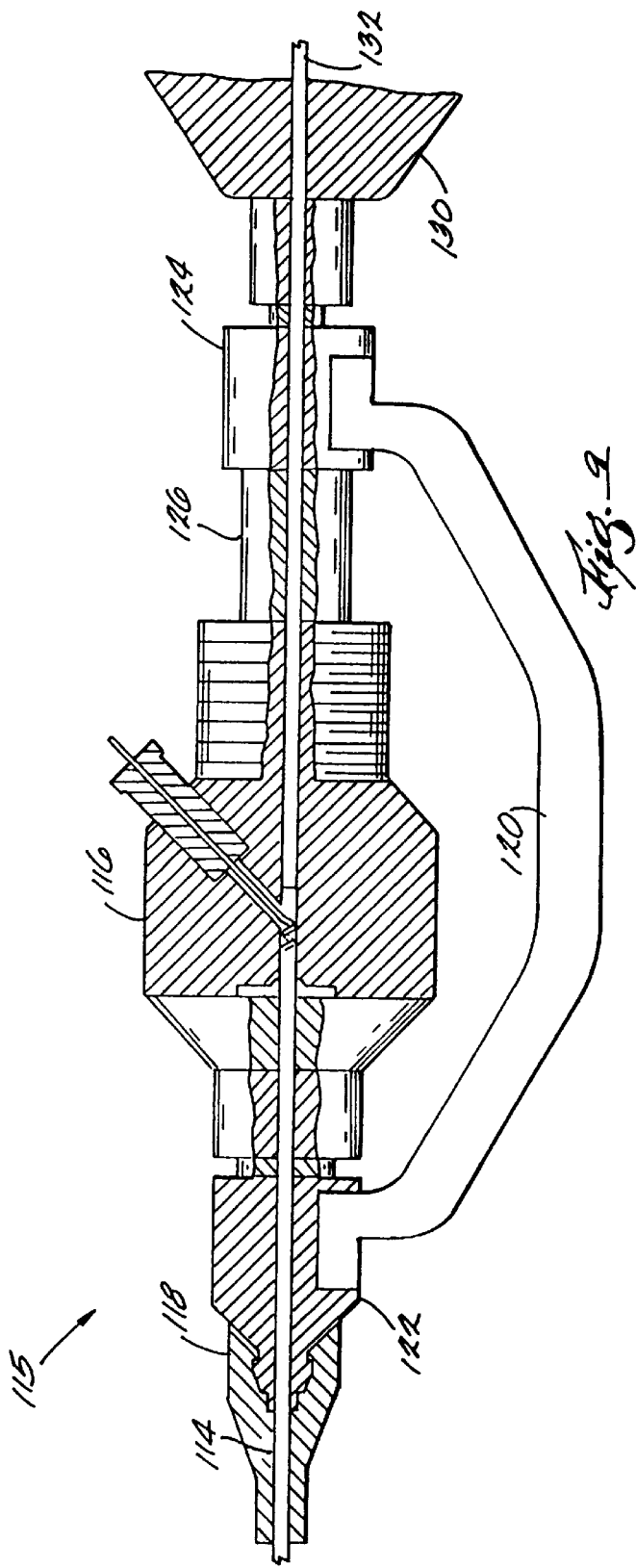

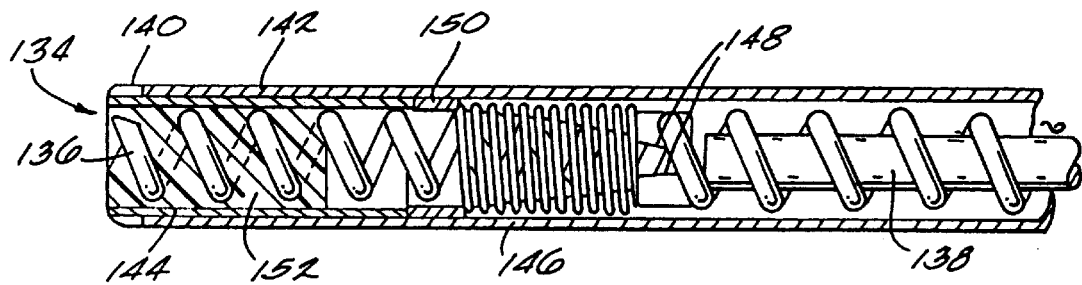
Fig. 10A
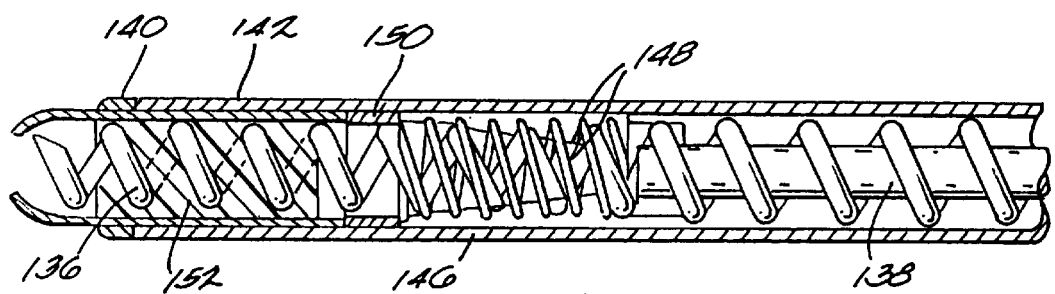
Fig. 10B
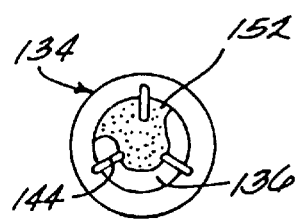
Fig. 10C
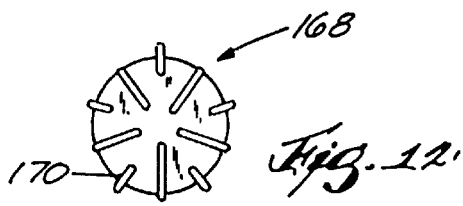
Fig. 12
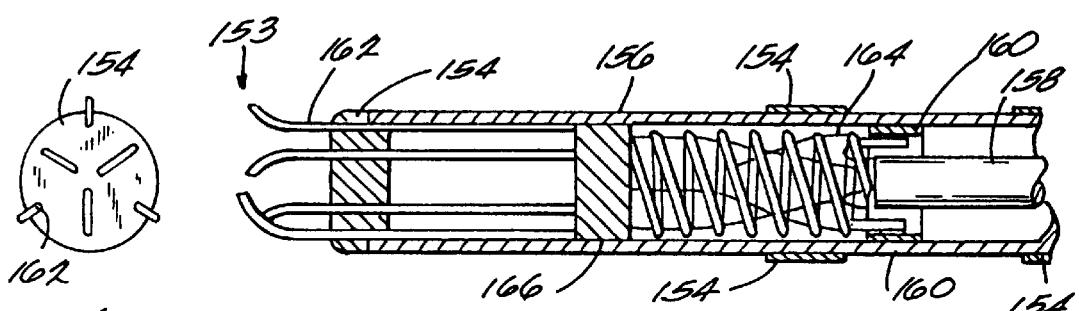
Fig. 11B
Fig. 11A

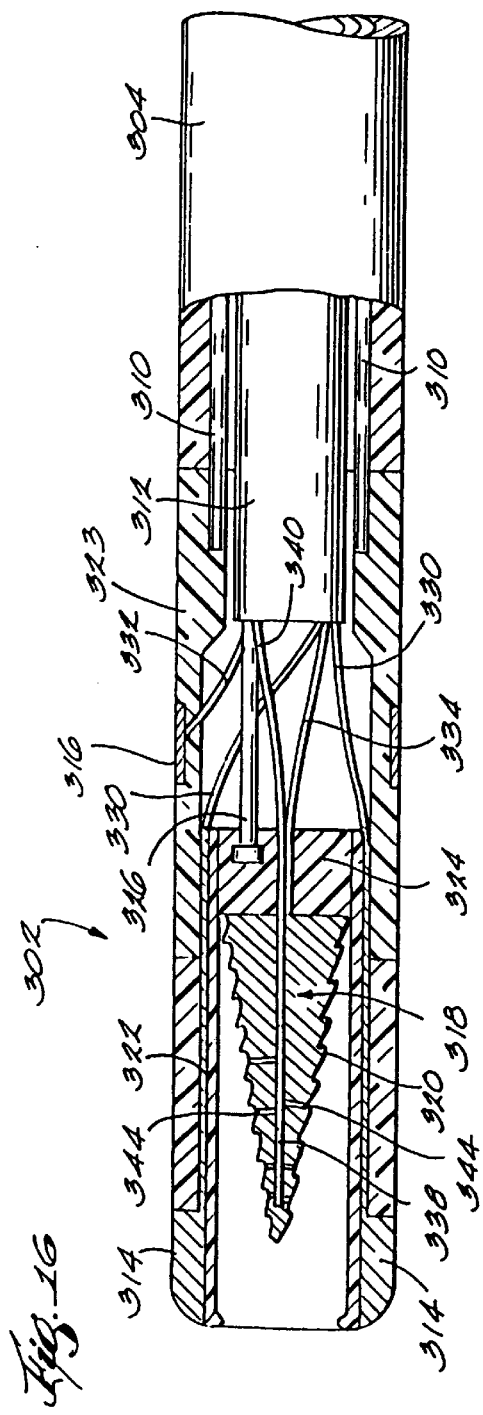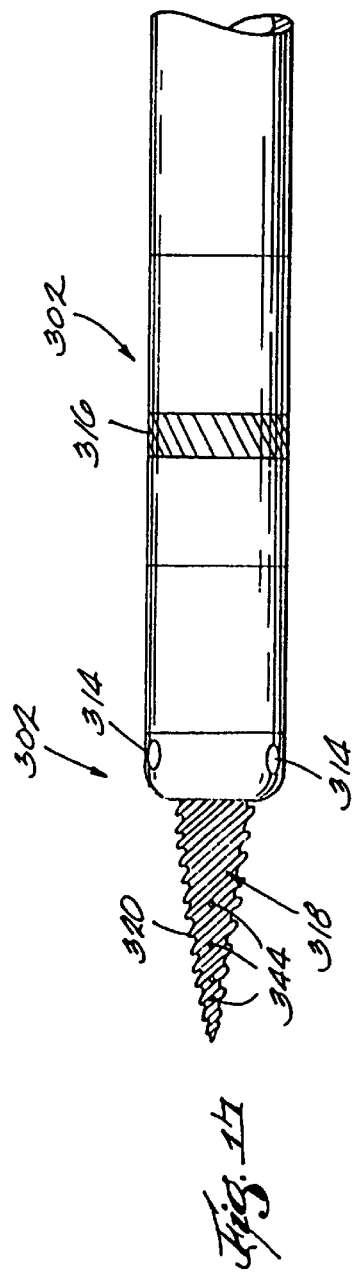

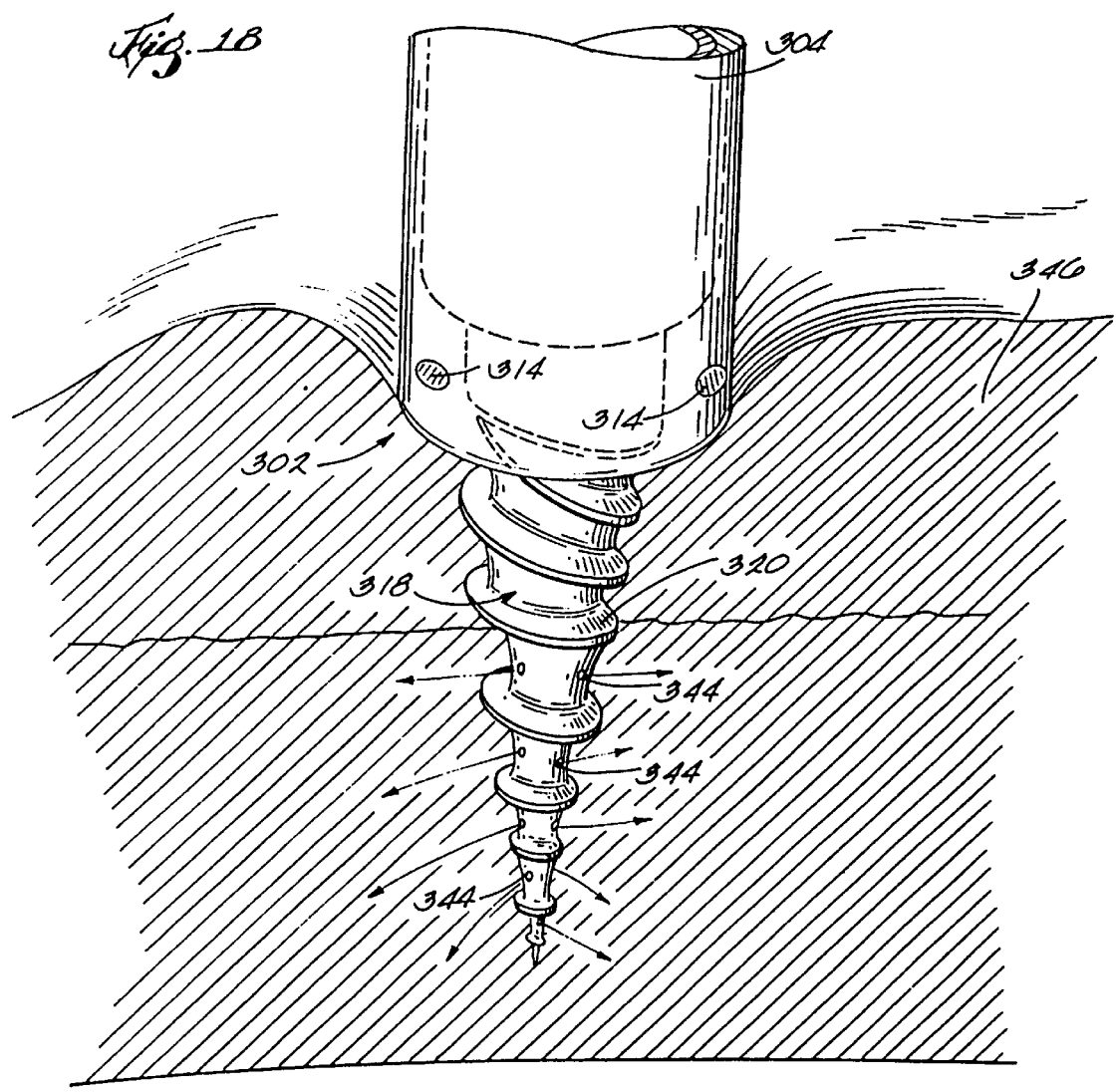

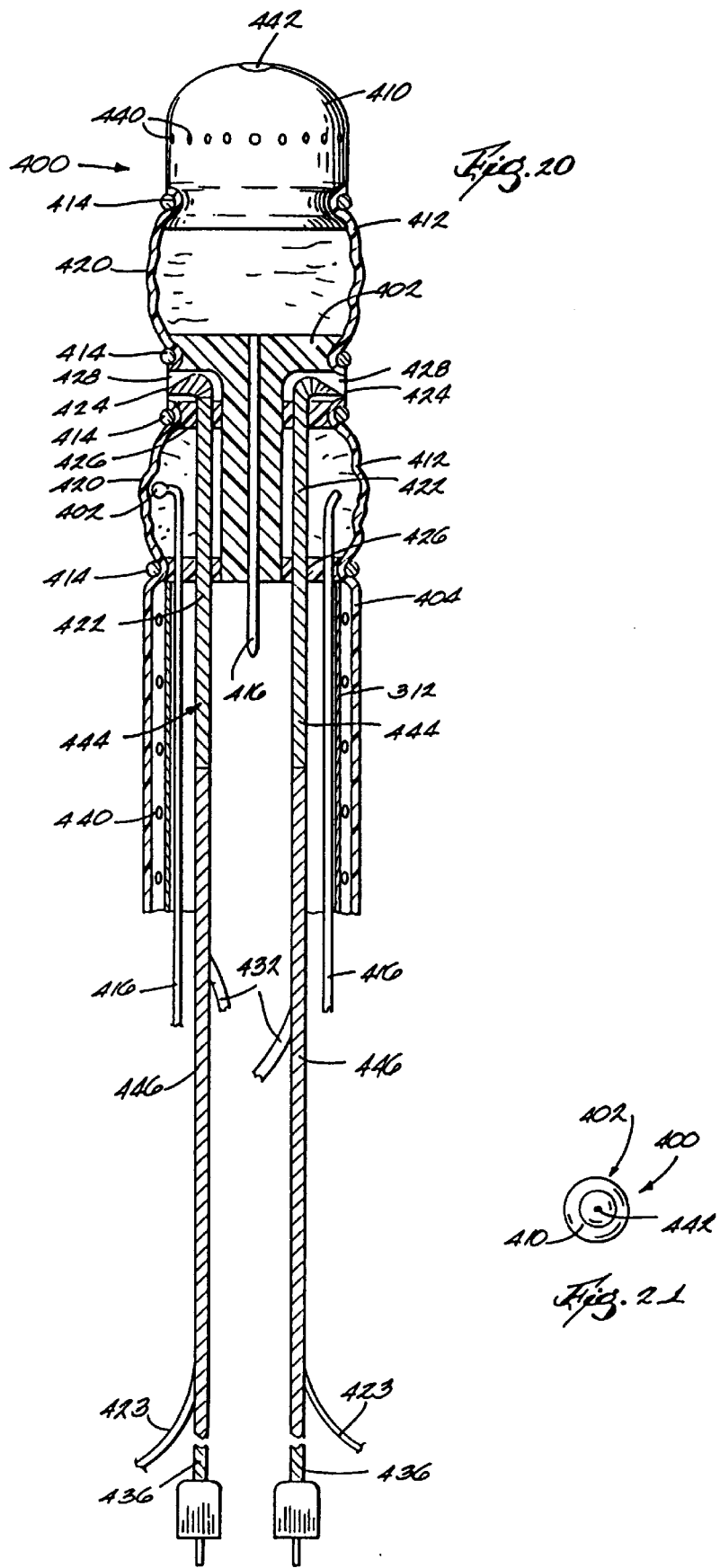

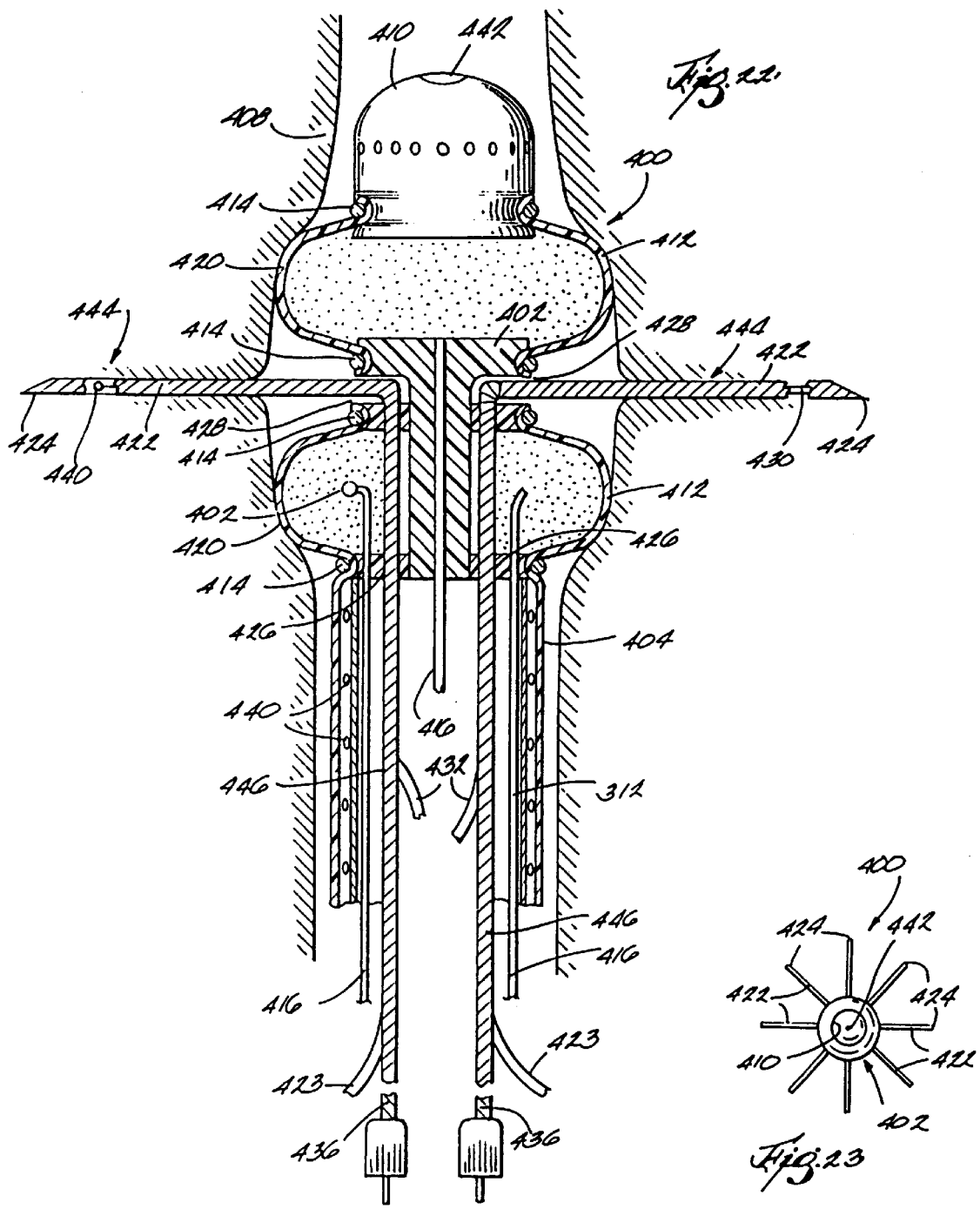

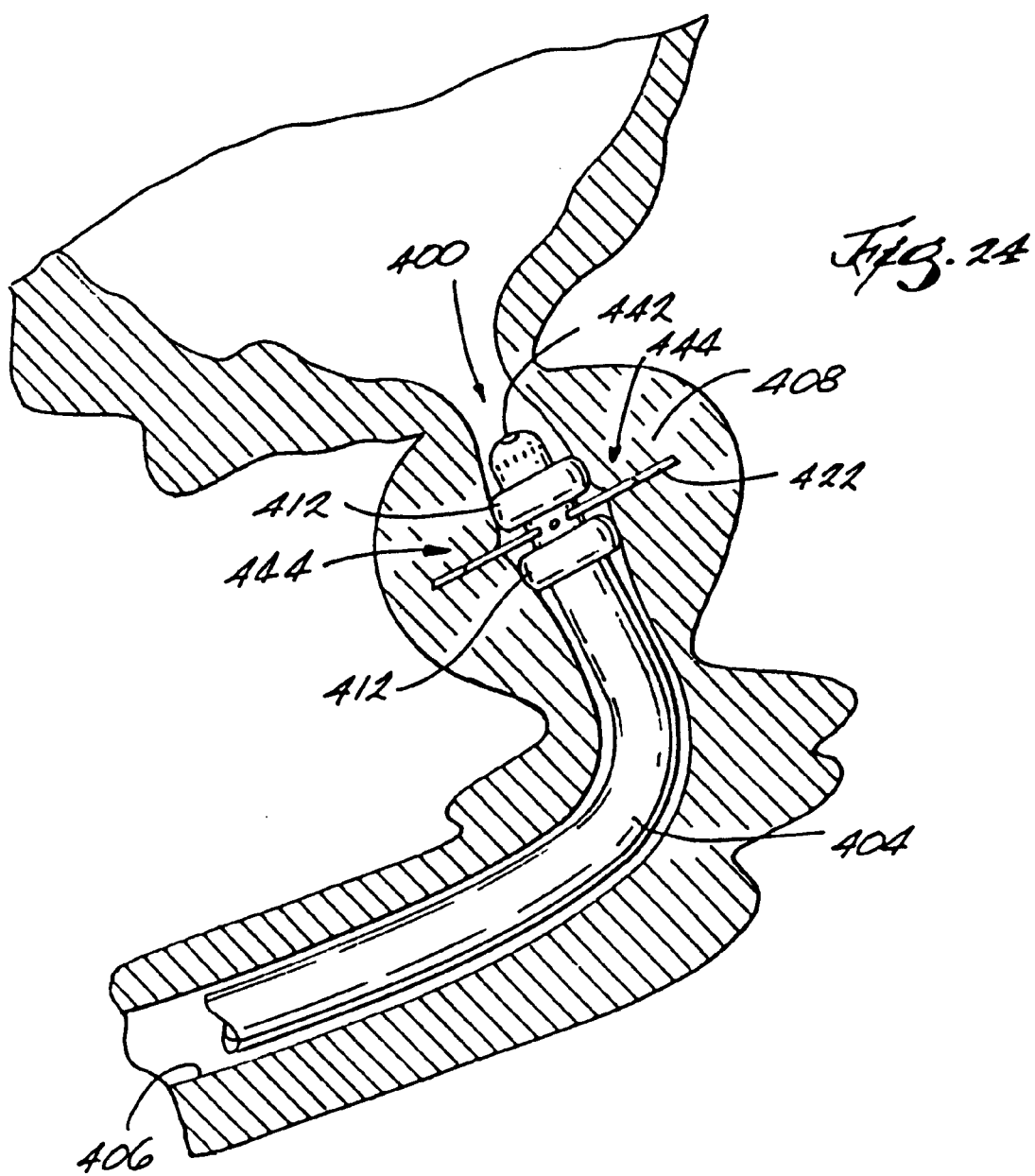

SYSTEMS AND METHODS FOR ABLATING BODY TISSUE

This is a continuation of application Ser. No. 08/315,396 filed on Sep. 30, 1994 (now abandoned); which is a continuation-in-part of application Ser. No. 08/100,086 filed Jul. 30, 1993 (now abandoned).

BACKGROUND OF THE INVENTION

Abnormal heart beats or cardiac arrhythmias can cause significant morbidity and mortality. These arrhythmias arise from a variety of causes, including atherosclerotic heart disease, ischemic heart disease, metabolic or hemodynamic derangements, rheumatic heart disease, cardiac valve disease, certain pulmonary disorders and congenital etiologies. The normal heart rate is about 60 to 100 beats per minute. Arrhythmias refer to tachycardias at rates exceeding 100 beats per minute for a duration of at least 3 beats. Sometimes no treatment is required, such as in the tachycardia following a physiologic response to stress or exercise. However, in some cases, treatment is required to alleviate symptoms or to prolong the patient's life expectancy.

A variety of treatment modalities exist, including electric direct current cardioversion, pharmacologic therapy with drugs such as quinidine, digitalis, and lidocaine, treatment of an underlying disorder such as a metabolic derangement, and ablation by either percutaneous (closed chest) or surgical (open chest) procedures. Treatment by ablation involves destruction of a portion of cardiac tissue which is functioning abnormally electrically.

Normally the heart possesses an intrinsic pacemaker function in the sinoatrial (SA) node which is in the right atrium, adjacent to the entrance of the superior vena cava. The right atrium is one of four anatomic chambers of the heart. The other chambers are the right ventricle, the left atrium, and the left ventricle. The superior vena cava is a major source of venous return to the heart. The SA node is an area of specialized cardiac tissue called Purkinje cells and which measures roughly 1-½ centimeters by about 2-½ millimeters. An electrical impulse normally exits from the SA node and travels across the atrium until it reaches the atrioventricular (AV) node. The AV node is located in the right atrium near the ventricle.

Emerging from the AV node is a specialized bundle of cardiac muscle cells which originate at the AV node in the interatrial septum. This "bundle of His" passes through the atrioventricular junction and later divides into left and right branches which supply the left and right ventricles. The left and right bundles further give rise to branches which become the so-called distal His-Purkinje system, which extends throughout both ventricles.

Thus in a normal situation an impulse originates intrinsically at the SA node, transmits through the atrium and is modified by the AV node. The AV node passes the modified impulse throughout the left and right ventricles via the His-Purkinje system to result in a coordinated heartbeat at a normal rate.

Many factors affect the heart rate in addition to the intrinsic conduction system. For example, normally the heart rate will respond to physiologic parameters such as stress, exercise, oxygen tension and vagal influences. Additionally, there are multiple causes for an abnormal heartbeat such as an abnormal tachycardia. One group of such causes relates to abnormalities in the heart's conduction system. For example, ectopic or abnormally positioned nodes may take over the normal function of a node such as the SA or AV node. Additionally, one of the normal nodes may be diseased such as from ischemic heart disease, coronary artery disease or congenital reasons. Similarly, a defect can exist in an important part of the conduction system such as the bundle of His or one of the bundle branches supplying the ventricles.

Treatment of abnormal tachycardias arising from ectopic foci or so-called ectopic pacemakers can include pharmacologic therapy or ablative therapy. The ablative therapy may be accomplished by percutaneous insertion of a catheter or by an open surgical cardiac procedure.

Cardiac arrhythmias may be abolished by ablating the tissue responsible for the genesis and perpetuation of the arrhythmias. Steerable ablation catheters using radio frequency (RF) energy are known. The RF energy can be directed to the area to be ablated and causes destruction of tissue by heat. In addition, direct infusion of ethanol has been performed during open heart surgery. Ethanol has also been infused into coronary arteries to ablate a focus such as a ventricular arrhythmia focus or the AV node. Unfortunately, this tends to result in a fairly large region of cardiac tissue death or myocardial infarction. With transarterial infusion there is difficulty in precisely controlling the location and extent of the ablation.

There are other conditions besides heart disease where tissue ablation by chemical or heat can achieve a therapeutic effect; for example, in the treatment of benign prostatic hypertrophy or hyperplasia (BPH).

SUMMARY OF THE INVENTION

The present invention is directed to systems and methods for ablating tissue in the body.

One aspect of the invention provides a medical probe device for contacting tissue within the body. The device comprises a catheter tube having a control end and a probe end. The probe end includes a housing having a port. An element is located within the housing. The element is movable between a first position confined within the housing and a second position extending through the port outside the housing. The element has a distal tip adapted to penetrate a tissue region during movement between the first and second position. The element comprises either an electrode for emitting electromagnetic radio frequency energy into the tissue region, or a cannula with an interior lumen for conveying fluid to and from the tissue region, or a sensor for sensing temperature conditions in the tissue region.

In one embodiment, the element has a threaded exterior with a distal tip adapted to penetrate a tissue region in response to rotation of the element during movement between the first and second position.

Another aspect of the invention provides a method for ablating tissue within the body. The method introduces a catheter tube having a control end and a probe end in the body. The probe end includes a housing and an element within the housing movable between a first position confined within the housing and a second position extending outside the housing. The element has a distal tip adapted to penetrate a tissue region during movement between the first and second position. During introduction into the body, the element is located in the first position within the housing.

The method places the probe end in contact with a tissue region and moves the element from the first position to the second position to penetrate the contacted tissue region. The method ablates the tissue region, while the element penetrates it, by either emitting electromagnetic radio frequency energy through the element into the tissue region or conveying ablation fluid through a lumen in the element for discharge into the tissue region.

For use in ablation of cardiac tissue, the catheters in one preferred embodiment of the invention have an elongated flexible body and a tissue ablation assembly having a tissue ablation tip at the distal end of the body. The distal end of the catheter is introduced into a cardiac chamber (or other body region) including the tissue to be ablated. The catheter may be equipped for standard arrhythmia mapping, for example multiple electrodes may be present on the outside of the catheter for recording endocardial electrograms. Alternatively, the catheter may include a visualization assembly at the distal end of the body. The visualization assembly is used to position the tip of the catheter adjacent the tissue to be ablated. Catheters comprising visualization and ablation means are described in copending application Ser. No. 08/099,995, Filed Jul. 30, 1993, entitled "Cardiac Imaging and Ablation Catheter," which is incorporated herein by reference.

In one embodiment, the tissue ablation assembly comprises a hollow infusion needle which can be extended or withdrawn from the distal end of the catheter. The hollow infusion needles of the invention have a securing element configured to engage tissue when the needle is at least partially inserted into the tissue to stop recoil and help prevent inadvertent removal of the needle from the tissue. The securing element can be configured into the form of corkscrew or threads surrounding a straight needle. Alternatively, the securing element can be configured as a plurality of pre-curved needles, which curve towards or away from the longitudinal axis of the catheter. The pre-curved needles can also be used to deliver ablation compounds if desired. Other structures, such as barbs, could also be used as the securing element. The hollow infusion needle is preferably a corkscrew-shaped needle, with a tight curl. The distance between turns is preferably about 0.5 mm or less. Such a needle allow the practitioner to inject through layers by slowly extending the needle, injecting, extending farther and injecting again.

When used to ablate tissue the catheter can be used with a conventional ablation compound such as alcohol (e.g., ethanol), collagen, phenol, carbon dioxide and the like. The solution may comprise various components for other purposes as well. For instance, an echocontrast agent for echo imaging may be included. Collagen can be bound to an iodinated molecule to make it radiodense. Alternatively, when used for gene therapy protocols, the catheters of the invention can be used to introduce desired polynucleotides to the target tissue.

When performing a percutaneous or closed chest cardiac ablation procedure using the catheters of the invention, fluoroscopy can be used to visualize the chambers of the heart. Fluoroscopy uses roentgen rays (X-rays) and includes use of a specialized screen which projects the shadows of the X-rays passing through the heart. Injectable contrast agents to enhance the fluoroscopic picture are well known in the art and are not described in detail here.

Typically, the catheter is placed in an artery or a vein of the patient depending on whether the left (ventricle and/or atrium) or right (ventricle and/or atrium) side of the heart is to be explored and portions thereof ablated. Frequently an artery or vein in the groin such as one of the femoral vessels is selected for catheterization. The catheter is passed via the blood vessel to the vena cava or aorta, also depending on whether the right or left side of the heart is to be catheterized, and from there into the appropriate atrium and/or ventricle.

The catheter is generally steerable and it is positioned against an endocardial region of interest. As mentioned above, the catheter typically includes a means for sensing the electrical impulses originating in the heart. Thus, the electrode catheter can provide a number of electrocardiogram readings from different areas of the internal aspects of the heart chambers. These various readings are correlated to provide an electrophysiologic map of the heart including notation of normal or abnormal features of the heart's conduction system. Once the electrophysiologic map is produced, an area may be selected for ablation.

Typically, before final ablation, the suspect area is temporarily suppressed or deadened with a substance such as lidocaine or iced saline solution. Subsequently the area is remapped and heart reevaluated to determine if the temporary measure has provided some electrophysiologic improvement. If improvement has occurred, then the clinician ma proceed with permanent ablation typically using ethanol.

In one aspect, the present invention provides the novel combination of tissue ablation and tissue imaging in a single catheter to permit ablation of tissue to be properly accomplished by the correct selection of the ablation site and monitoring and controlling the ablation of the tissue being destroyed. The invention is preferably used with imaging ultrasonic transceivers in an ablation catheter to provide real time assessment of lesion volume and to monitor the tissue being ablated. Alternatively, one or more A-mode ultrasonic crystals can be used. As used herein, a visualization means of the invention may be either an imaging or an A-mode ultrasonic device. One or more transponder can also be used to assist in localizing the catheter tip.

For use in treating BPH, the catheters in one preferred embodiment of the invention have ablation elements that move outward to penetrate tissue from the side of the probe. The ablation elements either emit electromagnetic radio frequency energy to heat and thermally destroy the penetrated tissue or convey an ablation fluid to chemically destroy the penetrated tissue.

Other features and advantages of the invention will appear from the following description in which the preferred embodiments have been set forth in detail in conjunction with the accompanying drawings.

BRIEF DESCRIPTION OF THE DRAWINGS

FIG. 4 is an overall view of an alternative catheter made according to the invention;

FIG. 8 is an enlarged, simplified cross-sectional view of the tip of a catheter with a hollow needle retracted;

FIG. 9 illustrates the handle assembly of a catheter of the invention;

FIG. 10A is an enlarged, simplified cross-sectional view of the tip of a catheter with the anchoring needles and hollow needle in the extended position;

FIG. 10B shows the extended anchoring needles after the triggering device has released the shuttle and the compression spring;

FIG. 10C is an end view of the distal end showing the position of the pre-curved anchoring needles after release;

FIG. 11A is an enlarged, simplified cross-sectional view of the tip of a catheter with the anchoring/infusion needles in the extended position;

FIG. 11B is an end view of catheter tip in FIG. 11A;

FIG. 12 is an end view of a catheter tip with 10 anchoring/infusion needles;

FIG. 16 is an enlarged section view of the multi-function probe, which the catheter shown in FIG. 15 carries at its distal end, with the associated screw ablation element located in its retracted position;

FIG. 17 is an enlarged view of the multi-function probe with the associated screw ablation element located in its extended position;

FIG. 18 is a perspective view of the screw ablation element shown in FIGS. 16 and 17 deployed in its extended position in tissue;

FIG. 20 is an ablation element suited for the treatment of benign prostatic hypertrophy, with its associated expandable ablation electrodes collapsed and its associated penetrating ablation electrodes retracted;

FIG. 21 is a top view of the ablation element shown in FIG. 20;

FIG. 22 is the ablation element shown in FIG. 20, with its associated expandable ablation electrodes inflated and its associated penetrating ablation electrodes extended and penetrating tissue;

FIG. 23 is a top view of the ablation element shown in FIG. 22; and

FIG. 24 is a diagrammatic view of the ablation element when deployed for use in the prostrate region of the body.

DESCRIPTION OF THE PREFERRED EMBODIMENT

Figure 1:
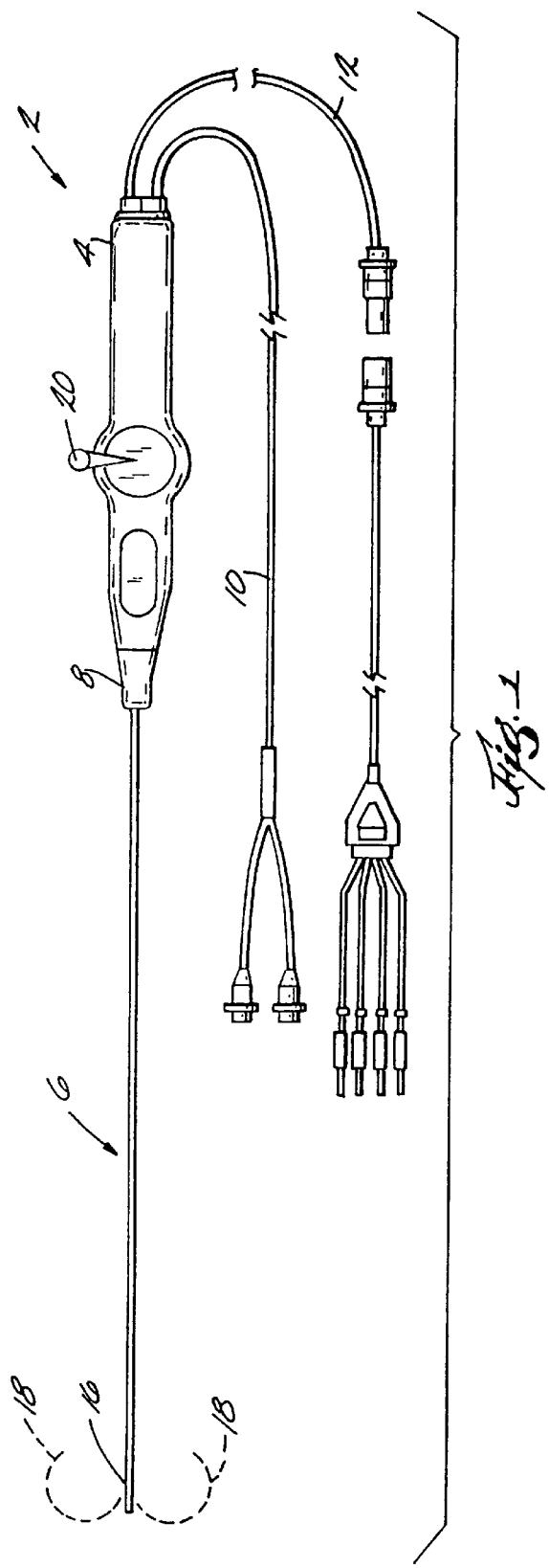
FIG. 1 is an overall view of a catheter made according to the invention.

FIG. 1 illustrates a catheter 2 having a handle 4 from which a flexible body 6 extends. Flexible body 6 extends from one end 8 of handle 4 while ultrasonic cable 10 and a combination electrode/thermistor cable 12 extend from the other end 14 of handle 4. Distal end 16 of flexible body 6 is steerable, as suggested by the dashed lines 18 in FIG. 1, in a conventional manner using a steering lever 20 mounted to handle 4. Lever 20 which controls one or more steering cables 22, see FIG. 2, as is conventional. Distal end 16 has an RF transmitting tip 24 secured thereto. Transmitting tip 24 is connected to an appropriate RF energy source, not shown, through lead 26 which extends along flexible body 6, through handle 4 and through combined cable 12.

Tip 24 has a pair of axially extending bores 28, 30 formed from its distal end 32. Bore 28 is used to house an ultrasonic transducer 34 while bore 30 is used to house a thermistor 36. Transducer 34 is surrounded by a thermal insulating sleeve 38, typically made of insulating material such as polyimide. The base 40 of transducer 34 has a lead 41 extending from transducer 34, along flexible body 6, through handle 4 and through ultrasonic cable 10. The ultrasonic transducer comprises a piezoelectric crystal capable of operating at a standard frequency, typically from about 5 to about 5 MHz. The crystal is formed from standard materials such as barium titanate, cinnabar, or zirconate-titanate. The transducer 34 generates an ultrasonic pulse in response to electrical impulses delivered through lead 41. Ultrasonic echoes are then received by the ultrasonic transducer 34 which generates electrical signals which are delivered to the receiving unit (not shown). The transducer is connected to conventional transmitting and receiving units which include the circuitry necessary for interpreting the ultrasonic information and displaying the information on a visual display. Signal processing may take advantage of change in tissue density or texture as correlated with lesion depth. The ultrasonic signal can be visualized on a two dimensional echocardiograph or using non-imaging A-mode.

Base 40 of transducer 34 is sealed with a UV potting adhesive 42, such as Tough Medical Bonder made by Loctite, to provide both thermal and electrical insulation. The catheter also comprises an ultrasonic transponder 44, shown schematically in FIG. 3, spaced about 2.5 mm from RF transmitting tip 24 at the distal end 16 of body 6. Transponder 44 is used to help in localization of the catheter tip as is known in the art and described in Langberg et al., *JACC* 12:218–223 (1988). In alternate embodiments, multiple transponders can be used to help with assessing catheter tip orientation as well.

Figure 3:
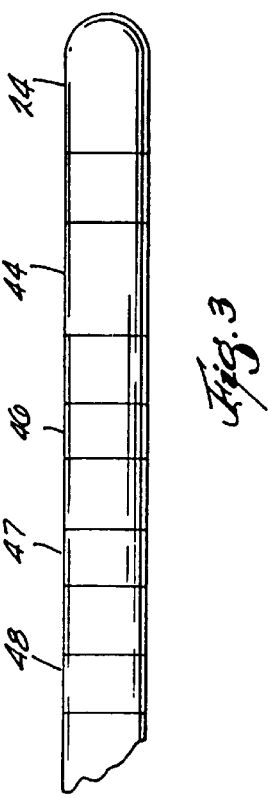
FIG. 3 is an enlarged, schematic cross-sectional view of the distal end of the flexible body of FIG. 1 illustrating the general locations of the tip electrode, ultrasonic transducer, and ring electrodes.
Figure 2:
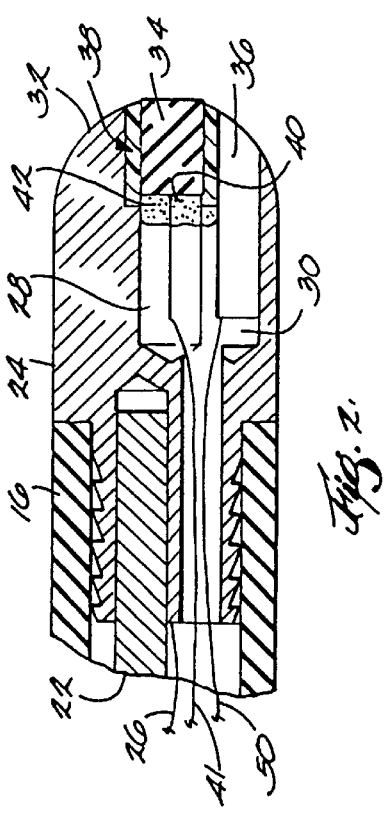
FIG. 2 is an enlarged, simplified cross-sectional view of the distal end of the flexible body of FIG. 1.
Figure 5:
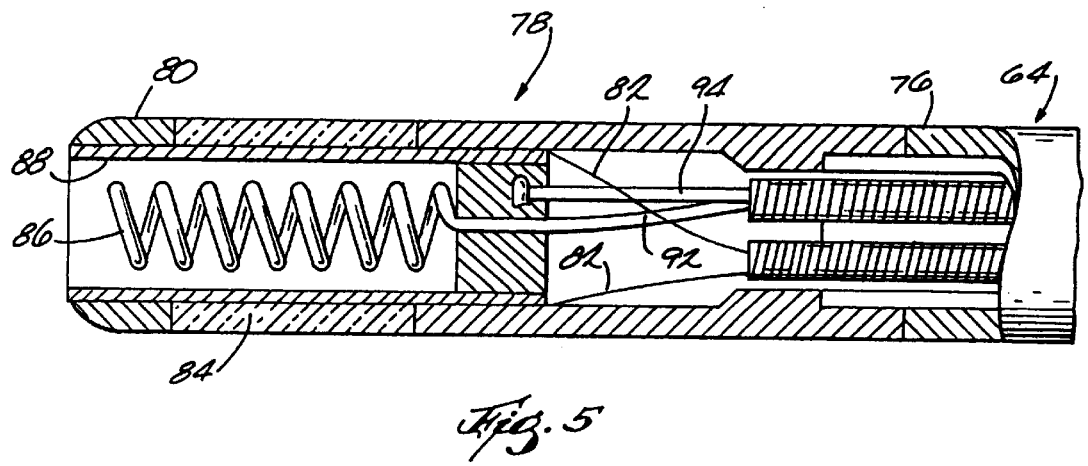
FIG. 5 is an enlarged, simplified cross-sectional view of the tip and the catheter of FIG. 4, shown with a hollow needle retracted.
Figure 6:
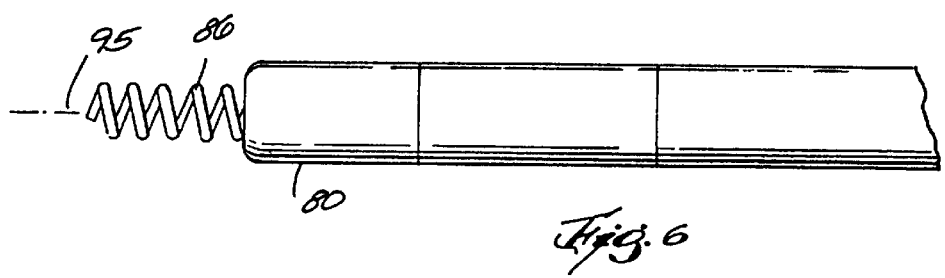
FIG. 6 is an external view of the tip of FIG. 5 with the hollow needle extended.
Figure 7:
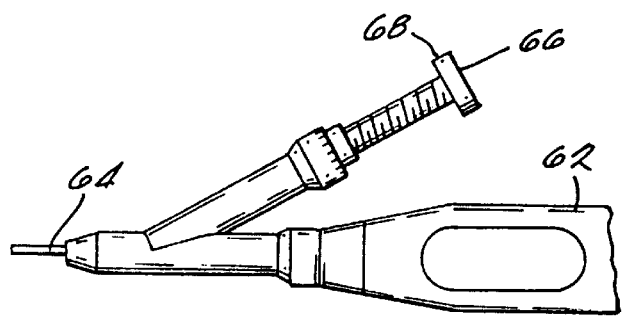
FIG. 7 is an enlarged view of the needle driver and infusion port mounted to the handle of FIG. 4.

In the embodiment of FIGS. 1–3, the ablation apparatus exemplified by the use of RF transmitting tip 24. In addition to tip electrode 24, catheter 2 also includes three ring electrodes 46, 47, 48 positioned in a proximal direction, that is towards handle 4 relative to tip electrode 24 and transducer 44. Electrodes 46–48 (spaced 2.5 mm apart) are used to record electrical signals produced by the heart (electrocardiograms) for endocardial mapping using a multichannel EKG machine as is known in the art. Thermistor 36 is coupled to combination cable 12 through a lead 50 extending from thermistor 36, to flexible body 6, through handle 4 and into combination cable 12. Thermistor 36 is used to provide information about the temperature of the tissue at the distal end 32 of tip 24.

Separately, the above-discussed apparatus used to create ultrasonic visualization of the tissue to be ablated is generally conventional. As discussed above, the ultrasonic visualization means may be used for either imaging or A-mode. One such ultrasonic imaging system is sold by Cardiovascular Imaging Systems of Sunnyvale, Calif. Similarly, the RF ablation system, used to ablate the tissue, is also generally conventional, such as is sold, for example, by EP Technologies, Inc. of Sunnyvale, Calif. What is novel is incorporating both the imaging and ablation structure into a single catheter which permits real time visualization and accurate positioning of the RF transmitter tip 24 with the precise location to be ablated. The amount or volume of tissue ablated can thus be constantly monitored during the procedure so that neither too little or too much tissue is ablated for maximum control and effectiveness. The use of temperature monitoring using thermistor 36 is also generally conventional as well, but not in conjunction with an ultrasonic imaging assembly. Instead of using RF energy to ablate the tissue, microwave radiation, laser energy, cryoblation or endocardial injection/infusion, for example, can be used in conjunction with ultrasonic transducer 34.

The use of catheter 2 proceeds generally as follows. Distal end 16 of body 6 is directed to the appropriate site using conventional techniques and steering lever 20. Visualization of the tissue to be ablated and localization of the tip 24 is provided by ultrasonic transducer 34, ultrasonic transponder 44, and associated leads and cables coupled to a conventional ultrasonic imaging console, not shown. When tip 24 is at the site of the tissue to be ablated, RF generator, not shown, coupled to combination cable 12, is activated to produce RF radiation at tip 24 to ablate the tissue. The ablation is monitored by ultrasonic transducer 34 as well as thermistor 36 to help ensure that the proper volume of tissue is ablated. When the proper volume of tissue is ablated, body 6 is removed from the patient. Instead of the use of catheter 2 including an RF transmitter tip 24, the catheter could use an ablation fluid infusion tip similar to that shown in FIGS. 4–7. Also, preparatory to the ablation sequence, the suspect area can be temporarily suppressed to deadened using catheter 60 using lidocaine or iced saline solution, as discussed in the Background section above.

Referring the reader now to FIGS. 4–7, a catheter 60 is shown. Catheter 60 includes a handle 62 from which a flexible body 64 extends. Handle 62 includes a steering lever 65 and combination infusion port 66 and needle driver 68 at the distal end 70 of handle 62. A pair of cables 72 extend from the proximal end 74 of handle 62. A pair of cables 72 extend from the proximal end 74 of handle 62. The distal end 76 of flexible body 64 has a tip assembly 78 mounted thereto. Tip assembly 78 includes mapping electrodes 80 connected to wires 82 which extend down flexible body 64, through handle 62 and to cables 72. Mapping electrodes 80 provide the user with a nonvisual indication of where tip assembly is by monitoring the electro-activity of the heart muscle, as is conventional. Electrodes 80 are electrically isolated from the remainder of tip assembly 78 by an insulating sleeve 84.

A hollow needle 86 is slidably mounted within a second insulating sleeve 88 housed within insulating sleeve 84. The needle may be formed from standard metal alloys such as titanium alloy, stainless steel, and cobalt steel. The needle 86 is a corkscrew-shaped needle used to inject ablating liquid into tissue and secure the needle to the tissue. Other designs of hollow needles, including the use of barbs on a straight or curved needle, can be used as well. While hollow needle 86 is shown used with a generally conventional mapping electrode type of catheter, it could be used with an ultrasonic visualization assembly as shown in FIGS. 1–3, as well as other types of visualization assemblies.

A central bore 90 of hollow needle 86 is coupled to infusion port 66 by an infusion fluid tube 92 which extends along flexible body 674, through needle driver 68 and to infusion port 66. Threaded needle driver 68 is connected to a tip extension 94 so that rotating needle driver 68 causes tip extension 94 to rotate about the axis 95 of needle 86 and to move axially within flexible body 64. This causes hollow needle 86 to rotate about axis 95 and to move axially within sleeve 88 from the retracted position of FIG. 5 to the extended position of FIG. 6.

Rotating needle driver 68 also rotates hollow needle 86 so that it bores into the tissue to be ablated. When properly in position, an appropriate liquid, such as ethanol, can be infused into the tissue to be ablated through infusion port 66, infusion fluid tube 92, hollow needle 86, and into the tissue. Since the tip 100 of hollow needle 86 is buried within the tissue to be ablated, the operator is assured that the ablation liquid is delivered to the proper place while minimizing ablation of surrounding tissue.

The needle is typically used to inject an ablation liquid endocardially to produce a more circumscribed lesion than that possible using prior art infusion techniques. The needle is designed such that it can be imbedded in and secured to the tissue to be treated.

Although ablation of cardiac tissue is a preferred use of the catheters of the invention, they can be used to inject desired compositions for a wide variety of uses. Virtually any therapeutic compound can be delivered intracardially using the catheters of the invention. For instance, the catheters can be used to deliver compositions comprising modified genes to cardiac or other tissue for use in gene therapy protocols. Methods for introducing a variety of desired polynucleotides to target cells using, for example, retroviral vectors are well known. Examples of sequences that may be introduced include antisense polynucleotides to control expression of target endogenous genes. In addition, genes encoding toxins can be targeted for delivery to cancer cells in tumors. In other embodiments, homologous targeting constructs can be used to replace an endogenous target gene. Methods and materials for preparing such constructs are known by those of skill in the art and are described in various references. See, e.g., Capecchi, *Science* 244:1288 (1989).

Other uses include intramyocardial delivery of isolated cells or cell substitutes. These approaches typically involve placement of the desired cells on or within matrices or membranes which prevent the host immune system from attacking the cells but allow nutrients and waste to pass to and from the cells (see, Langer et al., *Science* 260:920–925 (1993)). For instance, sinus node cells can be implanted in a desired location to treat disorders in impulse formation and/or transmission that lead to bradycardia.

Turning now to FIG. 8, the distal end 102 of a catheter of the present invention is shown. The hollow corkscrew infusion needle 104 is movably positioned within flexible distal tube 106. The flexible tube 106 allows movement of the distal end 102 in response to the steering mechanism 112. The steering mechanism 112 is conventional and functions as is known in the art. The distal end 102 also comprises mapping electrodes 108 which monitor electro activity of the heart muscle as described above. The mapping electrodes are connected through signal wires 111 to standard multichannel EKG machine as is known in the art.

The braided torque tube 114 is connected to the inside diameter of the infusion needle 104 and provides means for rotating the infusion needle 104 about the longitudinal axis 105 of the catheter and moving the needle 104 axially within the distal tube 106. The braided torque tube 114 consists of standard flexible tubing overlapped with a wire braid which stiffens the tube and allows torquing of the tube to rotate the needle 104.

FIG. 9 shows the handle assembly 115 of a catheter of the present invention. The braided tube 114 is connected to an infusion needle advance/retract knob 116 by which the user controls axial movement of the infusion needle 104. A female luer lock infusion port is positioned on the advance/ retract knob 116. A standard strain relief means 118 prevents kinking of the flexible tube 119. Also provided is a handle 120 secured to the catheter through front handle support 122 and rear handle support 124. The handle assembly 115 is attached to a standard steering/mapping catheter handle 130 as is conventional and signal wires 132 are connected to the appropriate receiving units.

FIGS. 10A through 10C show the distal end 134 of a catheter comprising an infusion needle 136 connected to a braided torque tube 138 as described above. The distal tube 142 also comprises an elastomeric seal 152 made from standard materials well known to those of skill in the art. The elastomeric seal 152 provides a seal for the distal tube 142 and prevents blood from flowing into the lumen of the catheter. Typically, the infusion needle 136 is coated with a compound such as mold release, to facilitate movement of the needle through the elastomeric seal 152.

Also included in this embodiment is a set of spring loaded pre-curved anchoring needles 144 positioned near the outer edge of the distal tube 142. The anchoring needles are attached to a shuttle 150 and compression spring 146 which are triggered through pull wires 148 through a trigger device on the handle. The function of the trigger device is shown more fully in FIGS. 13A, 13B and 14.

FIG. 10B shows the extended anchoring needles 144 after the triggering device has released the shuttle 150 and compression spring 146. This mechanism permits the distal end of the catheter to be attached in an almost instantaneous fashion and eliminates the effects of cardiac motion on the attachment procedure. FIG. 10C is an end view of the distal end 134 showing the position of the pre-curved anchoring needles 144 after release. In the embodiment shown here, the anchoring needles 144 are curved towards the longitudinal axis of the catheter. The anchoring needles 114, however, can be curved towards or away from the longitudinal axis.

FIGS. 11A and 11B show a further embodiment of the catheter comprising anchoring needles 162 which are used for infusion as well as anchoring. In this embodiment, the needles 162 are connected to infusion channel 160 through which the ablation liquid or other compound is delivered to the infusion needles 162. The infusion needles 162 are shown in the extended position after the shuttle 166 and compression spring 164 have moved the needles 162 axially through the distal tube 156. As with other embodiments, map electrodes 152 can be used to create an electro physiological map of the tissue. Braided tube 158 is used to anchor the compression spring 164. The infusion needles are curved outward as well as inward in this embodiment (FIG. 11B).

FIG. 12 is an end view of the distal end 168 of a catheter of the invention showing the arrangement of infusion needles 170 in which five needles project away from the longitudinal axis and five project toward the axis.

Figure 13A:
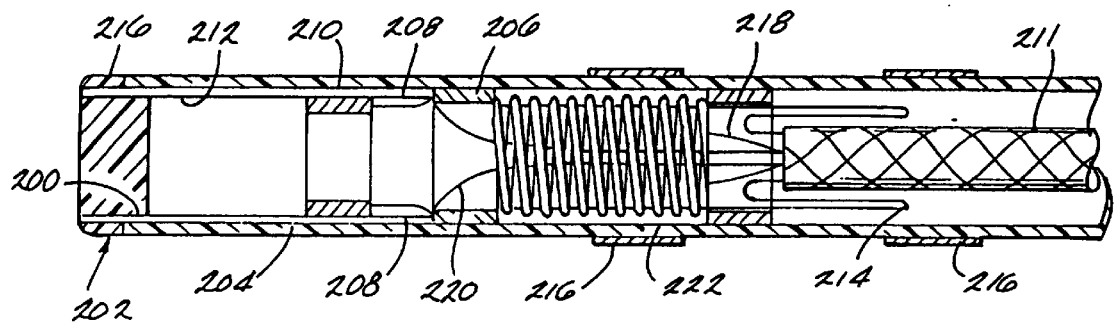
FIG. 13A is an enlarged, simplified cross-sectional view of the tip of a catheter showing the triggering mechanism with the anchoring/infusion needles in the retracted position.
Figure 13B:
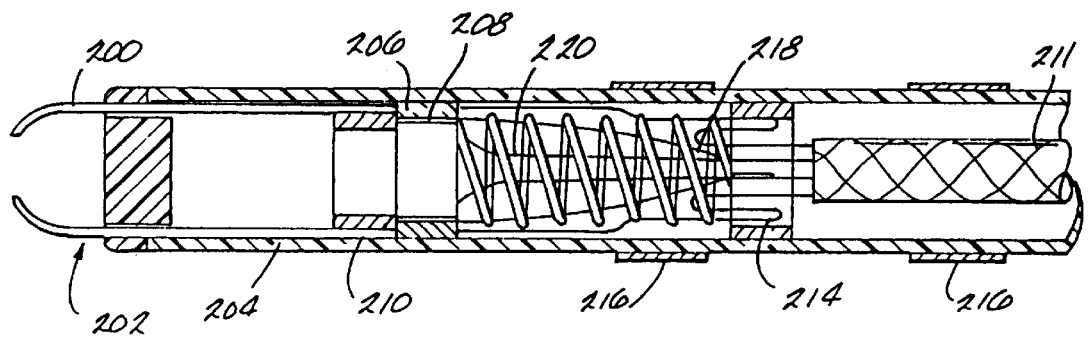
FIG. 13B is an enlarged, simplified cross-sectional view of the tip of a catheter showing the triggering mechanism with the anchoring/infusion needles in the extended position.
Figure 14:
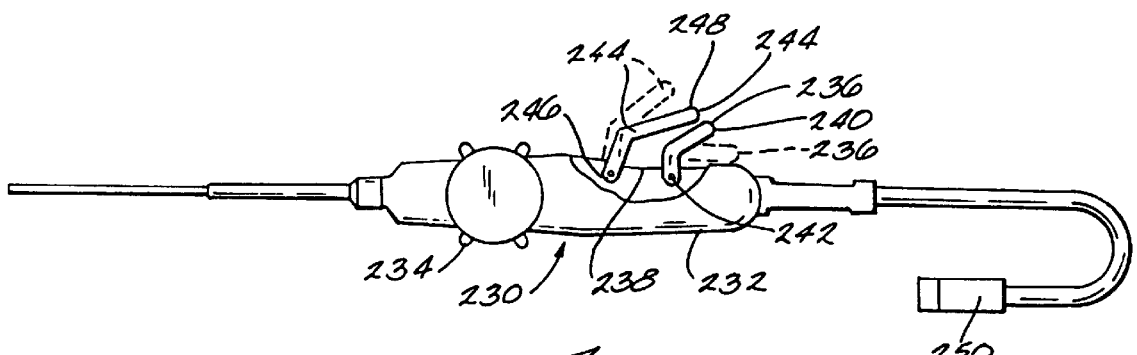
FIG. 14 illustrates the handle assembly of a catheter of the invention showing the trigger for releasing and retracting the anchoring needles.

FIGS. 13A and 13B illustrate the trigger assembly by which the pre-curved needles 200 ar released from the distal end 202 of the catheters of the present invention. FIG. 13A shows the pre-curved needles 200 in the retracted position within the flexible distal tube 204. The pre-curved needles 200 are attached to the shuttle 206 which is held in place by three trigger tabs 208, two of which are illustrated in FIG. 13A. The trigger tabs 208 are permanently fixed to the front stop 210 and pre-loaded against the inner diameter 212 of the distal tube 204.

As in the other embodiments disclosed above, the pre-curved needles 200 are fluidly connected to infusion channel 214, which enters the flexible distal tube distal 204, through braided tube 211. Map electrodes 216 are used to create an electro physiological map of the heart as described.

FIG. 13B shows the pre-curved needles 200 in the extended position after the trigger tabs 208 have been pulled towards the longitude axis of the catheter by the trigger pull wires 220. Once the trigger tabs 208 have been pulled towards the longitude axis, the shuttle 206 is released and the compression spring 222 drives the shuttle 206 and needles 200 rapidly towards the distal tip of the catheter. The inertia of the catheter body prevents the tip from withdrawing and needles 200 ar subsequently driven into the target tissue. FIG. 13B also shows the position of the trigger tabs 208 on the inner diameter of the shuttle 206 after the shuttle 206 has moved forward. After use the shuttle pull wires 218 are activated to pull the pre-curved needles 200 to the retracted position.

FIG. 14A shows the handle assembly 230 comprising a handle body 232 from which this position and ablation tip steering lever 234. The handle body 232 comprises a needle trigger 236 which is shown in both the cocked and fired (dashed lines) positions. The distal end of the trigger wires 238 are attached between the distal end 240 and the pivot point 242 to insure the wires 238 are pulled when the lever is pulled. The retractor 244 is shown in the cocked and fired (dashed lines) positions, as well. The pull wires 244 are attached between the pivot point 246 and the distal end of the retractor 248 as for the trigger. The handle assembly includes a lead 250 which allows for connection to appropriate ablation compound as described above.

Figure 15:
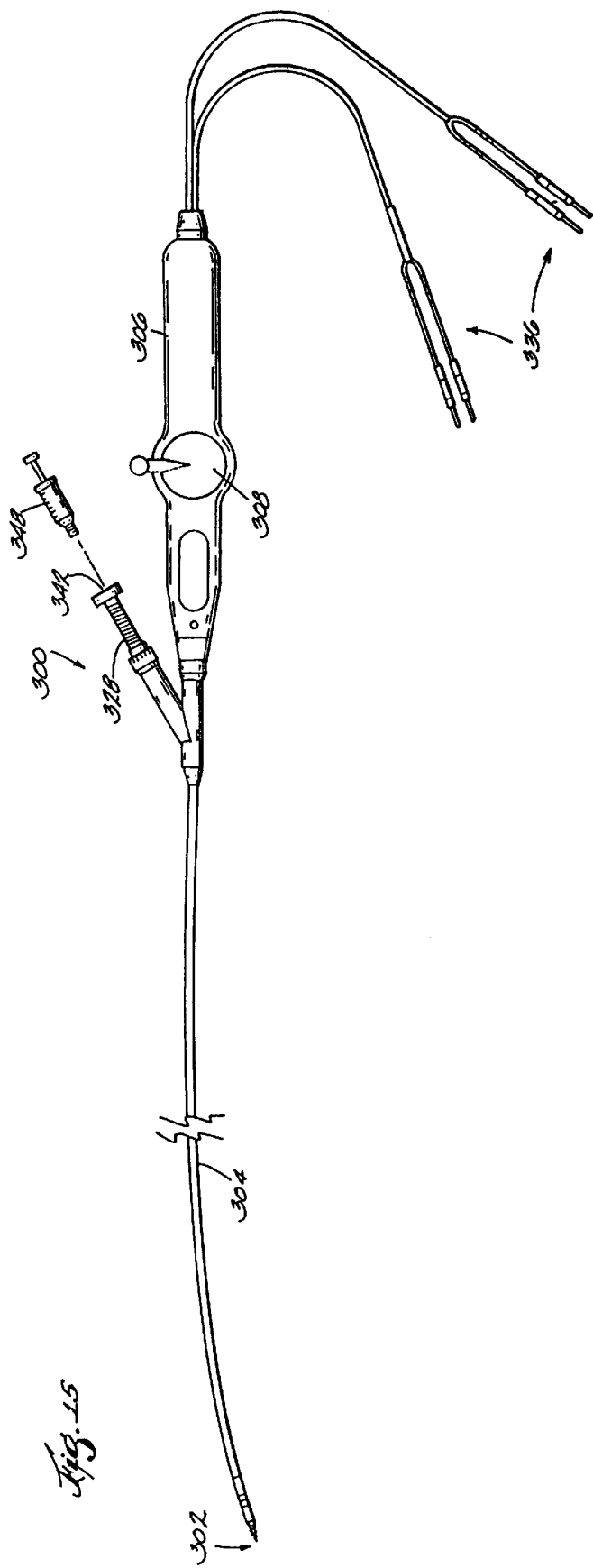
FIG. 15 is a catheter carrying at its distal end a multi-function probe that embodies the features of the invention.

FIG. 15 shows a catheter 300 having at its distal end a multi-function probe assembly 302 capable of sensing physiological events in endocardial and myocardial tissue, thermally stunning endocardial and myocardial tissue, and ablating myocardial tissue. The catheter 300 includes a conventional flexible guide coil 312 within a catheter tube 304 made of an electrically non-conducting material, like polyurethane (see FIG. 16). The proximal end of the catheter tube 304 carries a handle 306. The handle 306 allows the physician to remotely control the probe assembly 302 in the body.

Preferably, the distal end of the catheter tube 304 is steerable by conventional means, thereby also steering the probe assembly 302. For this purpose, the handle 306 carries a steering lever 308 attached by steering wires (not shown) to steering springs 310 in the distal end of the catheter tube 304 (see FIG. 16).

As FIGS. 16 and 17 show, the probe assembly 302 includes electrodes 314 and 316 that sense physiological events in heart tissue. In the illustrated embodiment, the electrodes 314 senses monophasic action potentials (MAP) in conventional fashion. The electrode 316 comprises the reference electrode for the MAP electrode 314.

The probe assembly 302 houses an ablation electrode 318. The ablation electrode 318 is made from a biocompatible material known to conduct electricity, like platinum or stainless steel. The electrode 318 is formed in the shape of a hollow screw. The electrode 318 will thus be called a "screw electrode." The screw electrode 318 includes a tapered or pointed exterior surface 320, which is sharpened for penetration of tissue. The surface 320 is also threaded, like, for example, a wood screw, for advancement into tissue when rotated.

A sleeve 322 guides and directs movement of the screw electrode 318 along an axial path within the probe assembly 302. The sleeve 322 is made of an electrically nonconductive material (like polyurethane) to thereby electrically insulate the screw electrode 318 from the MAP electrodes 314. The exterior of the probe assembly 302, except for the MAP electrodes 314 and reference electrode 316, is further enclosed by a sleeve 323 of electrically non-conducting material, which abuts against the catheter tube 304.

The base 324 of the screw electrode 318 is attached to a tip extending shaft 326. The shaft 326 passes through the guide coil 312 to a screw extender 328 on the handle 306 (see FIG. 15). Rotation of the screw extender 328 by the physician is translated by the shaft 326 into rotation and axial advancement of the screw electrode 318, which the sleeve 322 guides to move the screw electrode 318 between a retracted position within the probe assembly 302 (as FIG. 16 shows) and an extended position outside the probe assembly 302 (as FIG. 17 shows).

Insulated wires 330, 332, and 334 pass through the guide coil 312 for electrical connection to components of the probe assembly 302. The wires 330 and 332 are electrically coupled to the MAP electrodes 314 and the MAP reference electrode 316. The wire 334 is electrically coupled to the screw electrode 318.

The proximal ends of the wires 330, 332, and 334 pass into the handle 306. The wires 330, 332, and 334 are electrically coupled within the handle 306 to external connectors 336. The connectors 336 plug into a source of energy known to thermally destroy (i.e., ablate) body tissue. For example, microwave energy and other frequencies of electromagnetic radio frequency (RF) energy (lying in the frequency range of from about 500 kHz to about 2.5 GHz) are known to ablate body tissue. The wire 334 conveys the selected energy to the screw electrode 318 for transmission through tissue, when used in association with a conventional external patch electrode (called an "indifferent" electrode) attached to the patient's skin or to a grounding plate that the patient lies upon. The connectors 336 also plug into an external conventional device for processing the MAP signals, which are conveyed by the wires 330 and 332.

The screw electrode 318 also includes an interior passage or lumen 338 which communicates with an injection fluid tube 340. The injection fluid tube 340 extends through the guide coil 312 to an injection site 342 carried on the handle 306 (see FIG. 15). The interior passage 338 communicates with outlets 344 in the exterior surface 320 of the screw electrode 318 for discharging fluid carried by the injection fluid tube 340.

Figure 19B:
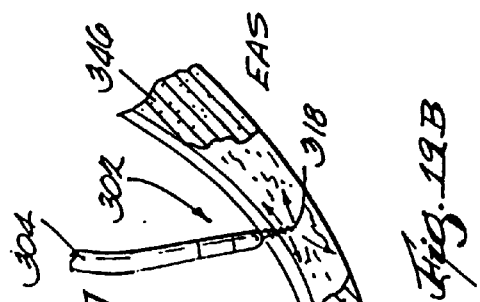
FIGS. 19A, B, C, and D are diagrammatic views showing the use of the multi-function probe shown in FIG. 15 in ablating tissue in the left ventricle of the heart.
Figure 19D:
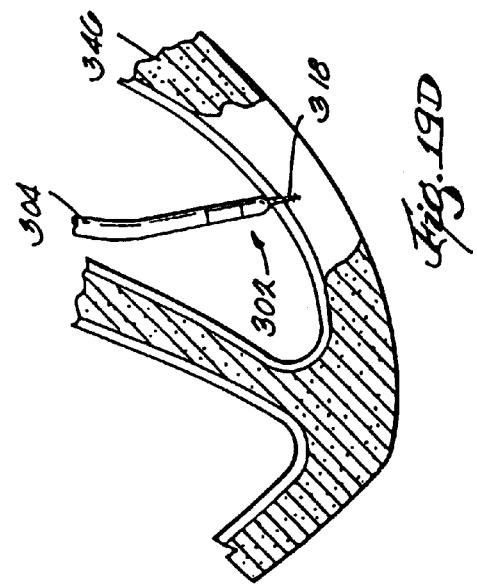
Figure 19A:
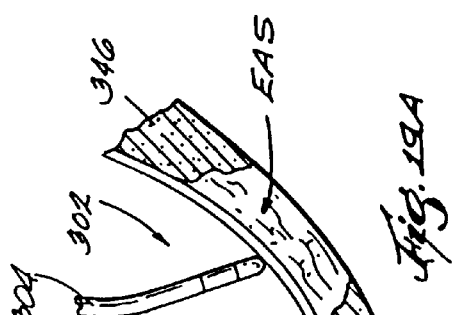

In use, the physician deploys the distal probe assembly 302 into the contact with tissue 346, which FIG. 19A diagrammatically shows to be within the left ventricle of the heart. With firm contact established, the physician uses the MAP electrodes 314 to measure MAP signals to locate an early activation site (EAS) using conventional techniques.

Once an EAS is located, the physician rotates the screw extender 328 to advance the screw electrode 318 into heart tissue where the EAS is found (as FIGS. 18 and 19B show). The physician injects very cold (iced) saline with a syringe 348 (see FIG. 1) through the injection site 342. The outlets 344 on the screw electrode 318 discharge the cold saline into the surrounding tissue 346 (shown by arrows in FIGS. 18 and 19B). Alternatively, the physician can introduce carbon dioxide through the injection site 342, which results in cooling (through Joule-Thompson expansion) at the outlets 344 of the screw electrode 318.

The cold temperature temporarily stuns the surrounding tissue 346. The stunning electrically isolates the tissue from the surrounding myocardium, during which time the tissue physiology emulates dead tissue. Confirming that a given tacharrhymia cannot be induced when tissue 346 is stunned validates that a correct site for ablation has been located.

Figure 19C:
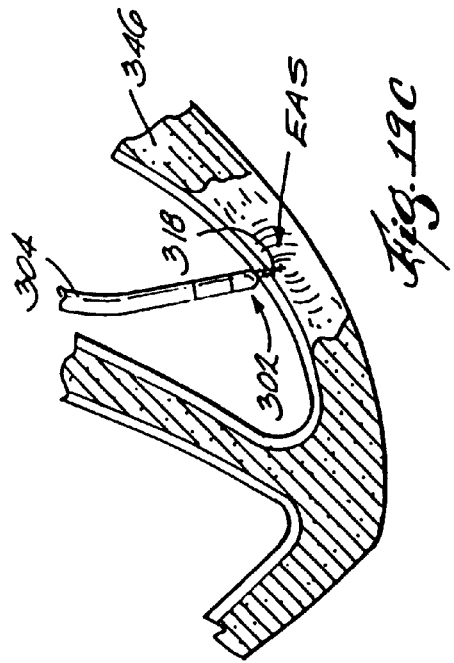

Next, without repositioning the probe assembly 302, and with the screw electrode 318 left imbedded in the tissue 346, the physician applies ablation energy to the screw electrode 318 for transmission into surrounding tissue (as the wave lines in FIG. 19C show). Since the screw electrode 318 is imbedded in tissue 346, the ablation energy reaches myocardial tissue significantly below the endocardium, deeper than a surface ablation electrode could reach.

As an alternative to RF ablation, the physician can inject alcohol through the injection site 342, which the outlets 344 on the screw electrode 318 discharge into the surrounding tissue area. The alcohol ablates the tissue by chemical means rather than by heating, as RF energy does.

The physician can validate the elimination of arrhythmia following ablation by reviewing endocardial electrograms. Once validation occurs, the physician rotates the screw extender 328 to withdraw the screw electrode 318 into its retracted position. The physician can withdraw the assembly 302 from the heart, or repeat the above steps, as necessary, to locate and eliminate multiple arrhythmia sources.

FIGS. 20 to 24 show an ablation element or probe 400 suited for the treatment of benign prostatic hypertrophy or hyperplasia (BPH). The ablation element 400 includes a body 402 attachable to the end of a conventional catheter tube 404 for insertion through the urethra (see FIG. 24) into contact with prostrate tissue 408. The catheter tube 404 itself can be like that shown in FIGS. 15 and 16, with a flexible guide coil 312 running through it and a handle 306 at its proximal end. The body 402 of the ablation element 400 is made of an electrically non-conducting material conventionally used for medical use catheters, for example polyurethane. The diameter of the body 402 is about 20 Fr., or larger.

The element 400 includes near its distal end 410 one or more expandable bellows 412. The bellows 412 are made of a biocompatible elastomeric material, like silicone rubber. The bellows 412 are attached by upper and lower fluid-tight lock bands 414 circumferentially about the body 402.

Fluid lines 416 extend within the body 402 and communicate with each bellows 412. The fluid lines 416 pass through the flexible guide coil 312 and exit the proximal end of the catheter tube 404 for attachment to an external source of saline solution (or another physiologically compatible liquid). The fluid lines 416 convey the solution from the external source into the bellows 412. As FIG. 22 shows, the fluid expands the bellows 412, urging them into contact with tissue 408. The fluid-filled bellows 412 stabilize the position of the element 400, while cooling the tissue 408 during ablation.

In the illustrated and preferred embodiment, the exterior surfaces of the bellows 412 are coated with an electrically conducting metal material 420, like platinum. Wires 423 (which pass through the flexible guide coil 312) electrically connect the metalized surfaces 420 to an external source of energy known to thermally destroy (i.e. ablate) body tissue. As before stated, microwave energy and other frequencies of electromagnetic radio frequency (RF) energy lying in the frequency range of from about 500 kHz to about 2.5 GHz are known to ablate body tissue. The bellows 412 emit the ablation energy conveyed by the wires 423. The bellows 412 thereby serve, when used in association with a conventional external patch electrode or grounding plate (as before described), as expandable electrodes to ablate tissue in the prostrate area for treating BPH.

The body 402 of the ablation element 400 houses an array of circumferentially spaced tubes 422. In use (see FIG. 22) the tubes 422 extend radially outward from the body 402. The tubes 422 are made of a conventional highly flexible, biocompatible material, such as a nickel-titanium alloy, stainless steel, and cobalt steel. The tubes 422 are tapered to form sharpened terminal ends 424 that, in use, penetrate the surrounding tissue. In the illustrated embodiment, the tubes 422 are located between the expandable bellows 412. The tubes 422 extend through the flexible guide tube 312, so that their proximal ends are accessible to the physician at the proximal end of the catheter tube 404.

The tubes 422 are carried in passages 426 within the body 402. The passages 426 extend axially along the body 402 and bend in a curved path to open radially at ports 428 in the side of the body 402. The passages 426 (in concert with the flexible guide coil 312) guide movement of the flexible tubes 422 within the catheter tube 404 and body 402, under the control of the physician. The tubes 422 flex within the passages 426, which direct the tubes 422 radially through the ports 428 and out the side of the body 402.

The tubes 422 can therefore be moved inside the body 402 (as FIGS. 20 and 21 show), retracted within the ports 428 away from tissue contact, during introduction of the element 400 into the patient's body. The tubes 422 can be selectively and individually deployed by the physician outside the ports 428 and into tissue along the side of the body 402 (as FIGS. 22 to 24 show).

The tubes 422 are hollow. They have open interior lumens 430 (see FIG. 22) that communicate with supply lines 432 that pass through the flexible guide coil 312 to the proximal end of the catheter tube 404 for connection to a source of saline (or another physiologic liquid). The tubes 422 discharge the liquid from the supply lines 432 into the surrounding tissue 408. By applying a vacuum through the supply lines 432, the tubes 422 also aspirate fluid from the surrounding tissue 408. The tubes 422 thus serve to flush and remove debris from surrounding tissue 408 into which they penetrate.

The tissue penetrating regions 444 of the tubes 422 (see FIG. 22) are conditioned to be electrically conducting. The remainder 446 of the tubes 422 that extend through the guide coil 312 to the proximal end of the catheter tube 404 are either made of electrically non-conducting material or, if not, otherwise shielded with electrically non-conducting material. The electrically conducting tube regions 444 are electrically coupled to supply lines 436 at the proximal end of the catheter tube 404. The supply line 436 couple to a source of energy known to ablate tissue, as already described. The electrically conducting tube regions 444 emit the ablation energy that the supply lines 436 conduct. The electrically conducting tube regions 444 thus also serve as penetrating tissue ablation elements.

In the illustrated embodiment, the tissue penetrating regions 444 of the tubes 422 (which, in the illustrated embodiment, are made from electrically conducting material) are machined with helical patterns. The supply lines 436 comprise coaxial cables with proximal connectors for coupling the helically machined regions 444 to a source of microwave energy. In this embodiment, the penetrating tube regions 444 therefore serve as microwave antennas that penetrate tissue and ablate the penetrated tissue for therapeutic benefits in treating BPH.

The ablation element 400 further includes various temperature sensing elements 440 to monitor temperature conditions surrounding the element 400. An array of multiple temperature sensing elements 440 is located circumferentially about the distal tip 410 of the element. One or more additional temperature sensors 440 are located on the body 402 in thermal contact with the fluid within the bellows 412. A temperature sensor 440 (for example, a fiber optic temperature probe) is located within all or some of the lumens 430 in the tubes 422. Additional temperature sensors 440 are situated along the body 402.

The ablation element 400 also includes an ultrasound transponder 442 on its distal end 410. The transponder 442 can be used in association with an ultrasound catheter (not shown) introduced into the patient's anus to locate the element 400 within the prostrate area of the body.

Modification and variation can be made to the disclosed embodiments without department from the subject of the invention as defined in the following claims.

We claim:

1. A medical probe device for contacting tissue within the body, the device comprising a catheter tube having an axis, a distal end, a proximal end, and a bore extending within the catheter tube along the axis between the distal end and the proximal end, an element movably carried in the bore, the element having a proximal end and a distal end, a control shaft having a first region coupled to the proximal end of the element and a second region at the proximal end of the catheter tube for manipulation by a user to rotate and axially advance the element within the bore without rotation of the catheter tube between a first position, in which the distal end of the element is confined within the bore, and a second position, in which the distal end of the element extends beyond the distal end of the catheter tube, the distal end of the element having a threaded exterior with a tip adapted to penetrate a tissue region in response to rotation and axial advancement of the element within the bore between the first position and the second position, the element including an interior lumen for conveying fluid to the tissue region, and a fluid passage within the bore having a distal end communicating with the interior lumen and a proximal end at the proximal end of the catheter tube adapted for connection to a source of fluid that ablates the tissue region.

2. A device according to claim 1 and further including means carried by the catheter tube for deflecting the distal end of the catheter tube.

3. A medical probe device according to claim 1, wherein the distal end of the element comprises an ablation electrode configured for penetrating into the tissue region and transmitting energy therein, and further comprising signal wires coupled to the electrode and configured for connection to a source of energy.

4. A method for ablating tissue within the body comprising the steps of introducing a catheter tube having an axis, a distal end, a proximal end, and a bore extending within the catheter tube along the axis between the distal end and the proximal end, an element movably carried in bore, the element having a proximal end and a distal end, a control shaft having a first region coupled to the proximal end of the element and a second region at the proximal end of the catheter tube for manipulation by a user to rotate and axially advance the element within the bore without rotation of the catheter tube between a first position, in which the distal end of the element is confined within the bore, and a second position, in which the distal end of the element extends beyond the distal end of the catheter tube, the distal end of the element having a threaded exterior with a tip adapted to penetrate a tissue region during rotation and axial advancement of the element within the bore between the first position and the second position, the distal end of the element comprising an electrode for transmitting electromagnetic radio frequency energy into the tissue region, and signal wires coupled to the electrode adapted for connection to a source of radio frequency energy, the element being in the first position during introduction in the body, placing the proximal end of the catheter tube in contact with a tissue region, manipulating the control shaft to rotate and axially advance the element within the bore, without rotating the catheter tube, from the first position to the second position to cause the distal end of the element comprising the electrode to penetrate the contacted tissue region, and ablating the tissue region, while the distal end of the element comprising the electrode penetrates it, by conveying electromagnetic radio frequency energy from the source through the signal wires for transmission by the electrode into the tissue region.

5. A method for ablating tissue within the body comprising the steps of introducing a catheter tube having an axis, a distal end, a proximal end, and a bore extending within the catheter tube along the axis between the distal end and the proximal end, an element movably carried in the bore, the element having a proximal end and a distal end, a control shaft having a first region coupled to the proximal end of the element and a second region at the proximal end of the catheter tube for manipulation by a user to rotate and axially advance the element within the bore without rotation of the catheter tube between a first position, in which the distal end of the element is confined within the bore, and a second position, in which the distal end of the element extends beyond the distal end of the catheter tube, the distal end of the element having a threaded exterior with a tip adapted to penetrate a tissue region in response to rotation and axial advancement of the element within the bore between the first position and the second position, the element including an interior lumen for conveying fluid to the tissue region, and a fluid passage within the bore having a distal end communicating with the interior lumen and a proximal end at the proximal end of the catheter tube adapted for connection to a source of fluid that ablates the tissue region, the element being in the first position during introduction in the body, placing the proximal end of the catheter tube in contact with a tissue region, manipulating the control shaft to rotate and axially advance the element within the bore, without rotating the catheter tube, from the first position to the second position to cause the distal end of the element to penetrate the contacted tissue region, and ablating the tissue region, while the distal end of the element penetrates it, by conveying ablation fluid through the fluid passage to the lumen for discharge through the distal end of the element into the tissue region.

6. A medical probe device for contacting tissue within the body, the device comprising a catheter tube having an axis, a distal end, a proximal end, and a bore extending within the catheter tube along the axis between the distal end and the proximal end, an element movably carried in the bore, the element having a proximal end and a distal end, a control shaft having a first region coupled to the proximal end of the element and a second region at the proximal end of the catheter tube for manipulation by a user to rotate and axially advance the element within the bore without rotation of the catheter tube between a first position, in which the distal end of the element is confined within the bore, and a second position, in which the distal end of the element extends beyond the distal end of the catheter tube, the distal end of the element having a threaded exterior with a tip adapted to penetrate a tissue region in response to rotation and axial advancement of the element within the bore between the first position and the second position, the distal end of the element comprising an electrode for transmitting electromagnetic radio frequency energy into the tissue region, signal wires coupled to the electrode adapted for connection to a source of radio frequency energy, and a seal in the distal end of the catheter tube through which the distal end of the element passes during rotation and axial advancement toward and away from the second position.

7. A medical probe device for contacting tissue within the body, the device comprising a catheter tube having an axis, a distal end, a proximal end, and a bore extending within the catheter tube along the axis between the distal end and the proximal end, an element movably carried in the bore, the element having a proximal end and a distal end, a control shaft having a first region coupled to the proximal end of the element and a second region at the proximal end of the catheter tube for manipulation by a user to rotate and axially advance the element within the bore without rotation of the catheter tube between a first position, in which the distal end of the element is confined within the bore, and a second position, in which the distal end of the element extends beyond the distal end of the catheter tube, the distal end of the element having a threaded exterior with a tip adapted to penetrate a tissue region in response to rotation and axial advancement of the element within the bore between the first position and the second position, the element including an interior lumen for conveying fluid to the tissue region, a fluid passage within the bore having a distal end communicating with the interior lumen and a proximal end at the proximal end of the catheter tube adapted for connection to a source of fluid that ablates the tissue region, and a seal in the distal end of the catheter tube through which the distal end of the element passes during rotation and axial advancement toward and away from the second position.

8. A device according to claim 6 or 7 and further including means carried by the catheter tube for deflecting the distal end of the catheter tube.

* * * * *